United States Patent [19]

Lyon et al.

[11] Patent Number: 5,035,692
[45] Date of Patent: Jul. 30, 1991

[54] HEMOSTASIS CLIP APPLICATOR

[75] Inventors: Russell R. Lyon, Ramona, Calif.;
Alan S. Tash, Westland, Mich.

[73] Assignee: Nicholas Herbert, Fullerton, Calif.; a part interest

[21] Appl. No.: 479,512

[22] Filed: Feb. 13, 1990

[51] Int. Cl.⁵ ............................................. A61B 17/00
[52] U.S. Cl. .................................. 606/143; 606/151; 227/901
[58] Field of Search ............................... 606/139–143, 606/151; 227/901, 902

[56]  References Cited
U.S. PATENT DOCUMENTS

| | | | |
|---|---|---|---|
| 4,217,902 | 8/1980 | March . | |
| 4,246,903 | 1/1981 | Larkin | 606/143 |
| 4,637,395 | 1/1987 | Caspar et al. | 606/143 |
| 4,791,707 | 12/1988 | Tucker | 606/143 |
| 4,796,627 | 1/1989 | Tucker | 606/143 |
| 4,821,721 | 4/1989 | Chin et al. | 606/143 |

Primary Examiner—Stephen C. Pellegrino
Assistant Examiner—Gary Jackson
Attorney, Agent, or Firm—G. Donald Weber, Jr.

[57]  ABSTRACT

A hand held applicator device for supplying hemostasis clips, on demand and in an operative condition, to properly grasp the skin of a patient thereby to perform a hemostasic operation. The applicator device includes a magazine portion for storing and supplying the clips and an operational portion for manipulating the clips.

33 Claims, 3 Drawing Sheets

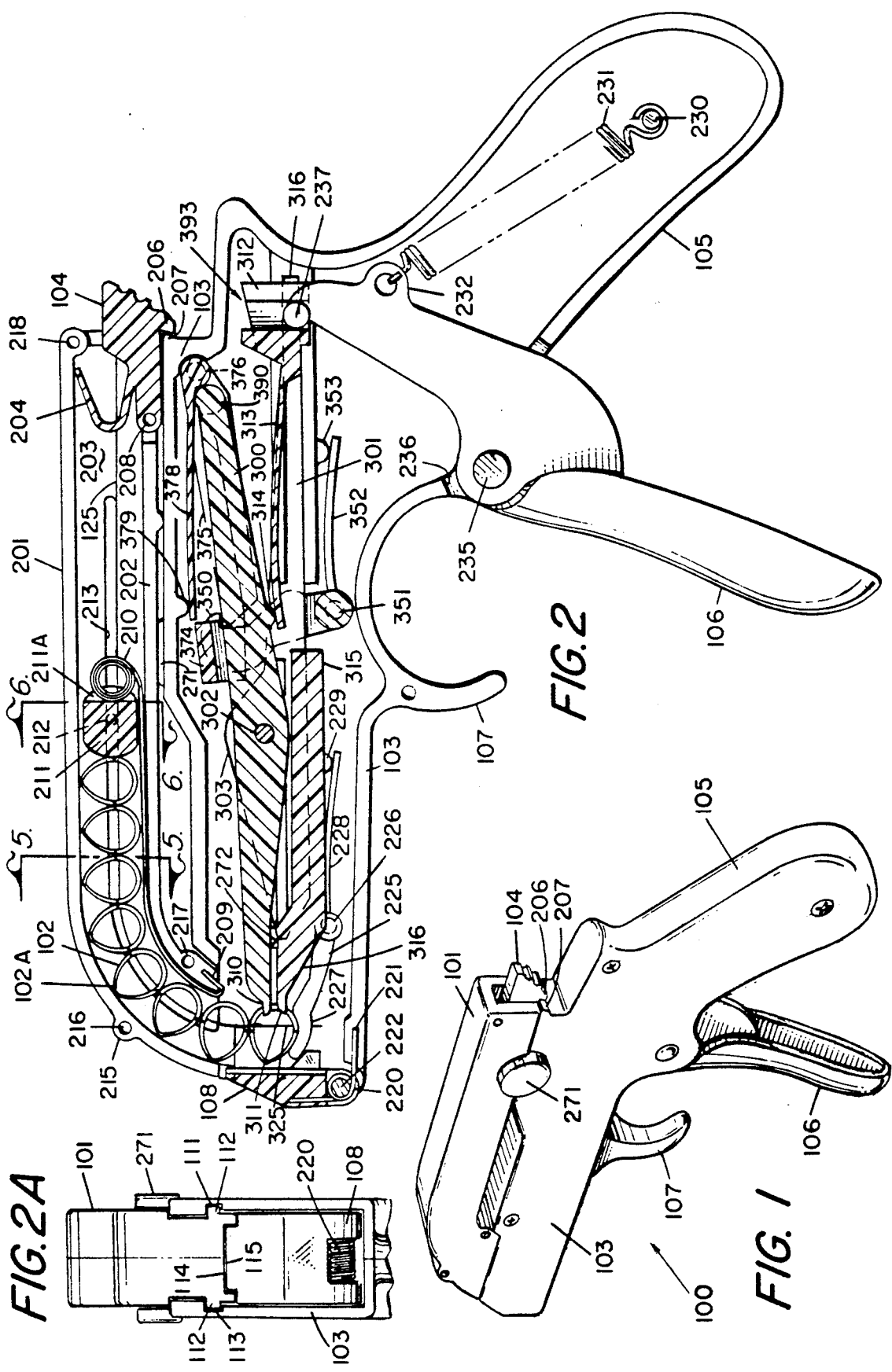

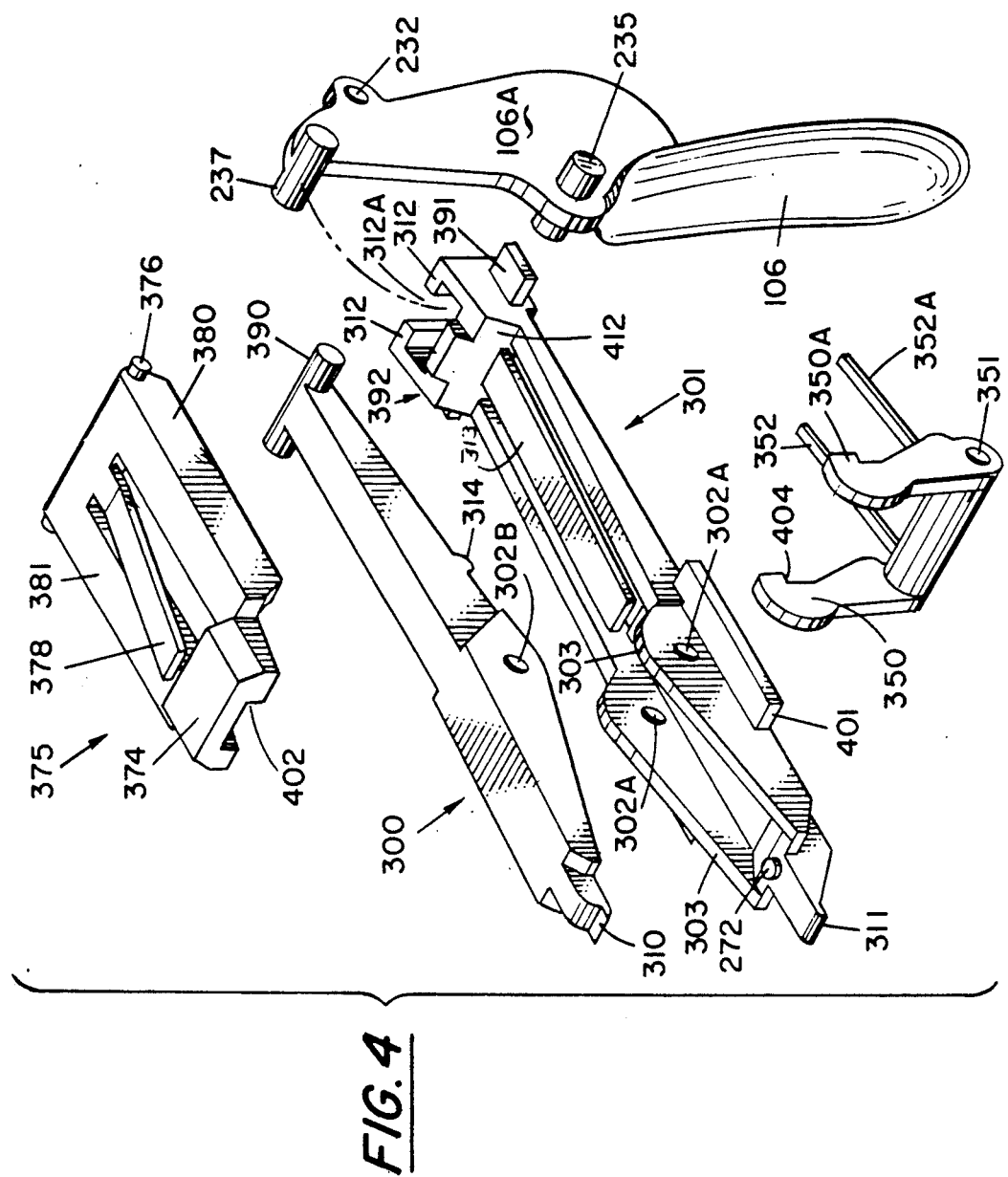

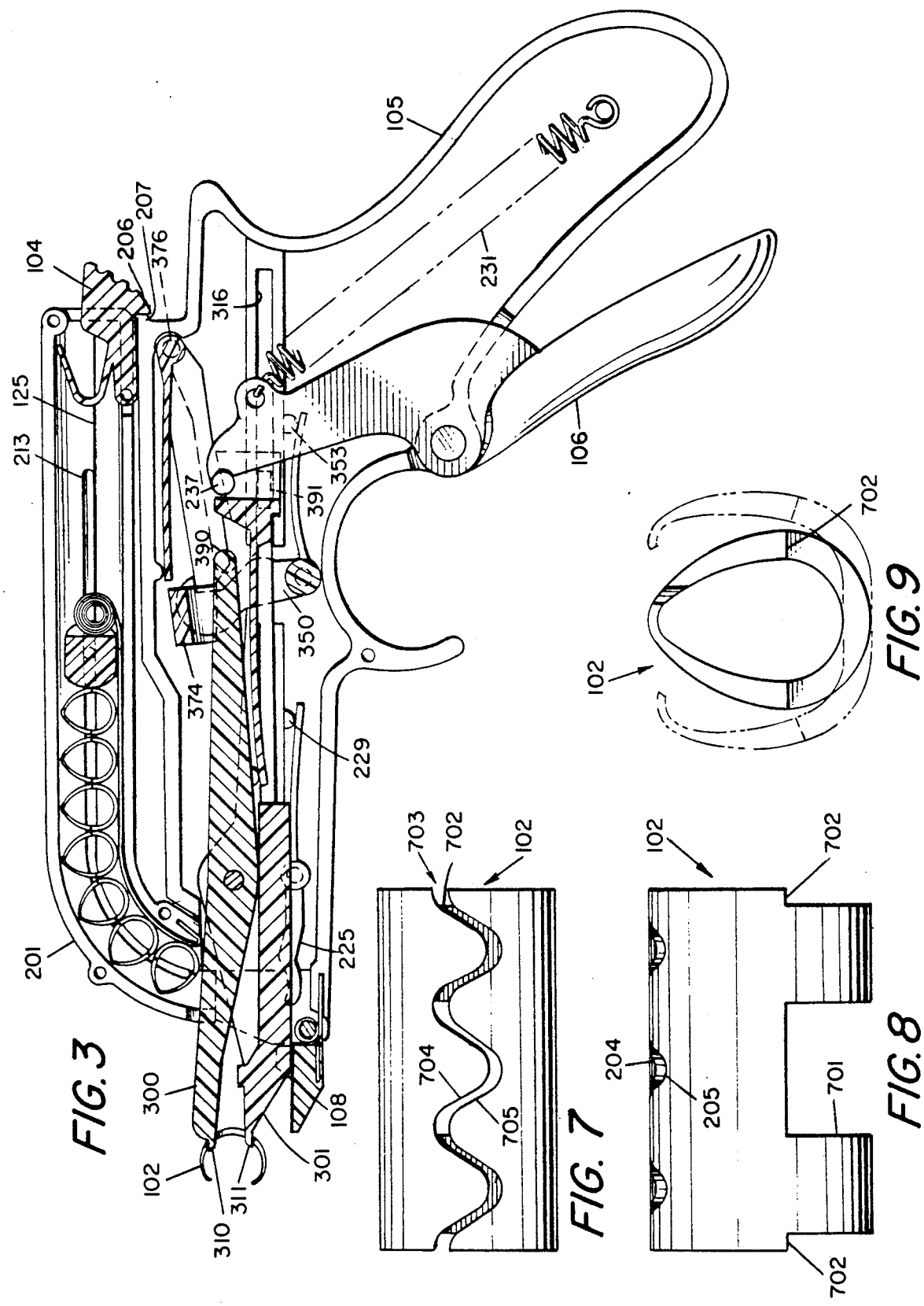

HEMOSTASIS CLIP APPLICATOR

BACKGROUND

1. Field of the Invention

This invention is directed to hemostasis clip applying means, in general, and to a hand held, gun-like device which retains a plurality of hemostasis clips and automatically dispenses same on demand, in particular.

2. Prior Art

In performing many medical procedures, it is necessary to make incisions. It is just as necessary to properly close the incision.

Also, in accidents, injuries and the like, it is frequently the case that the skin of a person is cut or torn wherein appropriate closure techniques and devices are required.

Over the years, new and different techniques have been used in order to assure that the edges of wounds are brought together and retained in that position until the wound is closed and healed. Initially, this was accomplished merely by use of appropriate bandages, tapes and the like. Later, stitching techniques were developed using, inter alia, cat gut filaments or the like. These materials were then subsequently replaced by other materials such as, but not limited to nylon, surgical steel or the like depending upon the nature of the wound, the severity thereof and the location relative to the body. In some instances, it is desirable that the stitching material is soluble in body fluids. This type of stitching is normally used in internal procedures.

Other types of closure devices include so called butterfly clips which may be formed of metal or plastic with prongs which become imbedded in the skin surrounding the wound.

In other types of surgical procedures, for example neurosurgical or cranial types of surgery, a skin flap is formed. That is, an incison is made in the scalp of the patient. Typically, this incision is in the shape of a horseshoe. The skin flap, for example at the inner portion of the horseshoe, may be elevated, for example, by a periosteal elevator and, thus, becomes a "free flap". However, because the scalp is heavily vascularized, considerable bleeding is usually encountered. In the past, this type of incision was merely cauterized to stanch the flow of blood during the procedure. The incision was then sutured in the usual fashion for closure.

Subsequently, other closure devices, referred to as hemostasis clips have been developed. These hemostasis clips, typically, are in the form of a rolled piece of plastic with a gap between the ends thereof. These ends include toothed or rugose edges thereof. The rolled plastic strip incorporates or includes a "memory" which, in essence, forces the edges of the clip together. Thus, in order to use these clips, the clips are individually expanded or opened by use of manual forceps or the like. This causes the edges of the gap in the clip to spread apart. The expanded clip is then placed over the edges of the skin flap and the clip is permitted to close. The memory of the clip produces a firm, forced closure thereof so as to inhibit bleeding at the incised edge of the skin flap.

A typical example of this type of clip is referred to as a Raney clip which is manufactured by Codman and Shurteff and others. In the type of surgical procedure, described above, "Raney" type clips are placed on the edges of the elevated flap. When the flap has been fully clipped, the surgeon returns to the still attached sides and clips them also. This clipping procedure insures hemostasis of the incision, and the surgeon is free to begin to open the skull.

The hemostasis clips have found acceptance in the operating room because they have numerous advantages insofar as being cheap, non-toxic, non-invasive and so forth. However, the clips as currently utilized have a distinct disadvantage in that they are applied individually, usually require two hands for application and are very time consuming to apply. Because of the time involved, there is the disadvantage to the patient of time on the operating table, loss of blood, slow response time (by medical personnel) in emergency situations, and the like.

Consequently, it is highly desirable to develop a means and/or technique wherein a plurality of the Raney-type clips can be placed in a condition of readiness and applied to the appropriate incision area quickly and efficiently.

PRIOR ART STATEMENT

There are no known issued patents relating to devices of the type shown and described and claimed hereinafter.

The most pertinent prior art known to Applicants is the so-called Caspar Scalp Clip System by Aesculap Werke Aktiengesellschaft of West Germany. However, this system applies so-called Caspar clips, not Raney-type clips, and operates on a completely different principle.

SUMMARY OF THE INSTANT INVENTION

This invention is directed to a hemostasis clip dispenser and applicator. The applicator is sometimes referred to as a "gun". A suitable handle or grip is provided, as well as a magazine for storing a plurality of the hemostasis clips therein. The clips are spring-loaded in the magazine to be biased toward a utilization location at the front end of the "gun". The trigger mechanism selectively permits a unit comprising upper and lower jaws to interact with an individual clip so that the clip is moved forwardly out of the gun. At the same time, the jaws tend to expand or spread the clip so that it can be applied in a normal or conventional manner, to the edge of the skin flap. The trigger is spring-loaded to the inactivated or closed position. Consequently, when the pressure is removed, the trigger is repositioned to the original position and, thereby, moves the jaws back into the gun housing. At that time, a spring-loaded guard or door at the front of the gun assumes the rest position and the spring-loaded clips are advanced to place another clip in position for subsequent operation.

BRIEF DESCRIPTION OF THE DRAWINGS

FIG. 1 is an external view of the hemostasis clip applicator of the instant invention.

FIG. 2 is a cross-sectional view of the hemostasis clip applicator of the instant invention in the rest or inactive position.

FIG. 2A is a partial end view of the front end of the applicator of the instant invention.

FIG. 3 is a cross-sectional view of the hemostasis clip applicator of the instant invention in the activated or operational position.

FIG. 4 is an exploded view of the jaw members and related internal components of the instant invention.

FIG. 5 is a cross-sectional view of the magazine portion of the instant invention taken along the lines 5—5 in FIG. 2.

FIG. 6 is a cross-sectional view of the magazine portion of the instant invention taken along the line 6—6 in FIG. 2.

FIG. 7 is an edge view of the toothed edge of the improved hemostasis clip used with the applicator of the instant invention.

FIGS. 8 is a side view of the improved hemostasis clip of the instant invention.

FIG. 9 is an end view of the improved hemostasis clip of the instant invention.

DESCRIPTION OF A PREFERRED EMBODIMENT

Referring now to FIG. 1, there is shown an exterior view of the hemostasis clip applicator 100 of the instant invention. The applicator 100 is sometimes referred to as a hemostasis clip gun because of the generally pistol-shaped configuration of the device.

The applicator 100 includes a magazine 101 which is adapted to retain a plurality of hemostasis clips 102 (see FIG. 2). The clips 102 are, generally, of conventional design. In particular, the hemostasis clips which are intended to be used with this apparatus are similar to those clips which are referred to in the trade as "Raney Clips". The conventional clips are made by Codman and Shurtleff, Weck and, perhaps others. However, as will become apparent, an improved or modified version of the so-called Raney-clip is used in the preferred embodiment of this invention.

A plurality of clips 102 are loaded into the magazine 101 individually or in a group. The magazine 101 is arranged to rest upon and latch to the upper surface of the applicator housing 103. A latch 104 is mounted at the back end of the magazine 101 and engages a lip 206 at the upper surface of housing 103. The curved, forward portion of the magazine 101 is placed in abutment with and latched to the delivery location in the housing 103.

A suitable pistol grip handle 105 is provided for handling and holding the applicator 100. The trigger 106 is pivotally mounted in the handle 105 and is operative to control the operation of the applicator 100 by selectively moving internal jaw components shown and described infra. The trigger guard 107 is used to provide a resting or support portion or area for the hand of the operator. Thus, a portion of the operator's hand can be used to hold the applicator while the other fingers of the hand are used to squeeze the trigger 106. A spring-loaded guide or door 108 (see FIGS. 2 and 2A) is mounted at the front of the applicator 100 and is selectively opened (see FIG. 3) in order to permit hemostasis clips 102 to be moved outwardly from the housing and readied for use in the clipping process. Positioning ears 271 are formed at the outer edges of the housing 103 to retain the magazine 101 in position.

Referring now to FIG. 2, there is shown a cross-sectional view of the applicator 100 of the instant invention in the rest positon. In this cross-sectional view, the internal components of the applicator are shown, as well. Thus, it is seen that the magazine 101 includes an upper track 201 and a lower track 202 together with a pair of side walls 203. The upper and lower tracks are essentially parallel to each other. Likewise, the side walls are parallel to each other, as well. The tracks and sidewalls form a generally rectilinear hollow tube.

While not essential, the magazine 101 is typically formed of transparent plastic material so that the clip contents can be readily observed. The forward end of magazine 101 is curved or turned in such a way as to direct the clips to the prescribed delivery location in housing 103. The rearward end of the magazine 101 is, generally, closed. However, a latch member 104 is pivotally mounted thereat.

The latch 104 includes a knurled or serrated outer surface which can be easily and readily moved by applying pressure with the thumb or other finger of the user. The latch 104 is selectively moved against the leaf spring 204 or living hinge which is, preferably, formed as an integral part of the latch 104. In this embodiment, the latch 104, pivots around the pivot pin 208. When the latch 104 is in the position shown, the bottom ledge 206 thereof is spring-loaded (by spring 204) against the upper portion of the housing 103 and engages lip 207 which extends therefrom. Thus, the latch 104 operates to positively engage the magazine 101 with the housing 103. Conversely, a separate leaf spring, coil spring or the like could be utilized.

At the front end of the magazine 101, the ends of the sidewalls 203 are configured to interface with and engage a portion of the housing 103. For example, and referring concurrently to FIG. 2A, the magazine 101 may include a groove 111 or projection 112 on each side of the forward end thereof. These projections are arranged to interact with and slideably engage counterpart grooves 113 in the inner front surfaces of the housing 103. (Of course, the grooves and projections can be reversed with the groove in magazine 101 and the projections on the housing 103, if desired.) The interlocking grooves and projections provide a juncture between the magazine 101 and the housing 103. Moreover, the housing 103 and magazine 110 are maintained in a preferred orientation to assure the proper delivery of the clips 102 to the applicator apparatus. Likewise, the forward end of upper track 201 may include a gap 114 which cooperates with lip 115 of door 108 as described infra.

On the other hand, the front end of the lower track 202 includes a slot 209 therein. One end of a rolled or coiled leaf spring 210 is inserted into the slot 209 and maintained therein by appropriate crimping, adhesives, or the like. The coiled leaf spring 210 extends along the lower track of the magazine until a coil is formed by whatever amount of the spring is not dispensed on the surface of the lower track. The coiled leaf spring 210 tends to rewind and, therefore, bears against the pusher block 211 and urges the pusher block (and the clips 102) forwardly.

The pusher block 211 has a slightly curved front surface to avoid any inadvertent hang-ups on the inner surfaces of the upper or lower tracks. The rear surface of the pusher 211 includes a vertical groove 211A therein to retain the leaf spring 210 in the proper configuration and cooperative engagement with the pusher 211.

In addition, the pusher block 211 includes a pin 212 which extends from either side of the pusher block 211 and rides in the channels 213 formed in the side walls 203 of the magazine 101. While only one side wall 203 and, thus, only one channel 213 is shown, it is understood that for better operation, a channel 213 on each side of the magazine is preferred.

A plurality of hemostasis clips 102 is mounted within the magazine. The clips 102 are normally individually provided and loaded into the magazine. However, it is contemplated that a plurality of the clips may be joined together by a tacky adhesive or other suitable, breakaway arrangement.

Typically, the open ends 102A of the clips are disposed upwardly while the apertured end of the clips are adjacent to the lower track 202. Moreover, the clips 102 include an undercut side which rides on the shoulder 125 which extends inwardly into the magazine 101. Typically, shoulder 125 is disposed beneath the guide channel 213 noted above. The clips are described in greater detail relative to FIGS. 7, 8 and 9, infra. Moreover, the shoulder 125 orients the clips 102 properly while they are moving through the magazine 101.

A projection 215 at the upper and outer surface of the magazine 101 inludes an aperture 216 therein. Similarly, an aperture 217 is provided in the forward portion of the bottom of the magazine. A similar aperture 218 is provided in the upper rear corner of the magazine 101. In addition other such apertures may be incorporated but are not shown. These apertures are intended to mate with and engage counterpart prongs which are formed in the other half of the magazine. The prongs and apertures are used to join the halves of the magazine 101 together. These components can be glued, laser welded or the like to form a permanent fixture, if necessary or desirable. (Of course, the elements 216, 217, and/or 218 can represent the prongs which mate with counterpart apertures in the other half of the magazine 101.)

The housing 103 is also constructed of a pair of cooperating sides or halves. The housing 103 includes a relatively flat upper surface which abuts and supports the lower track 202 of the magazine. The upper surface may be stepped in order to better accomodate the curved configuration of magazine 101. A positioning ear 271 is formed at the outer surface of each half of the housing 103 to retain the magazine 101 in position.

A handle 105 is formed at one end of the housing 103. The handle is substantially hollow and includes a boss 230 or similar means of anchoring one end of an elongated tension coil spring 231. The other end of the coil spring 231 is attached to an eye 232 which is formed adjacent the inner end of the trigger 106. The trigger is pivotally mounted on the trigger pivot pin 235 which is inserted into an aperture in the housing handle. Of course, the pivot pin can be formed as a boss in the housing and the trigger can include an aperture therethrough. The trigger 106 is adapted to pass within an aperture 236 formed when the two halves of the handle are joined together. Also formed at the inner end of the trigger 106 is a cross-bar 237 (or cylinder) which extends from each side of the trigger and engages the rear end of lower jaw means 301 (described in detail infra).

Thus, the trigger 106 is free to move rotatably about the trigger pivot 235. The spring 231 tends to bias the trigger to the rest position shown in FIG. 2. When the trigger is operated to move the lower jaw 301, as described infra, the spring 231 is extended. When the trigger is released, the spring 231 returns the trigger to the position shown.

A door 108 is provided at the front end of the housing 103. The door 108 is spring-loaded to the closed position as shown in FIGS. 2 and 2A. Coil spring 220 has one end embedded in the door and the other end embedded in a slot 221 in the lower portion of the housing. The coil spring 220 and the door 108 are mounted on a suitable pivot pin 222 which is mounted in the front end of the housing in suitable fashion. Thus, door 108 can be rotated about pivot pin 222 by (or against) action of the spring 220.

A pair of clip locator arms 225 are mounted on respective locator arm pivots 226 which are formed in each half of the housing 103. The clip locator arms 225 are spaced apart from one another and disposed adjacent the side walls of the housing 103. The forward end of each locator arm 225 includes an arcuate pad 227 which is adapted to receive the hemostasis clips 102 when they are placed in position adjacent to the door 108. The pad 227 is slightly arcuately shaped in order to complement the shape of a hemostasis clip 102 and to provide a secure rest position therefor. The other end of each locating arm 225 is a flexible, resilient arm 228 which extends toward the rear of the gun housing. A boss 229 is formed in at least one half of the housing against which the extended arm 228 of the locating arm abuts in a spring-loaded fashion. Thus, the locator arm 225 is biased to the rest position. However, the locator arms 225 are selectively rotated about pivot 226, and out of the operational area, during the application of a clip. Due to the resilience of extended arm 228, locator arm 225 returns to the rest position of the operation of the gun, as shown.

The clip manipulating apparatus includes a scissors or forceps-like unit. This unit includes an upper jaw 300 and a lower jaw 301. The upper jaw is pivotally mounted to the lower jaw in a suitable fashion by means of pivot 302. In the preferred embodiment, the lower jaw 301 includes a pair of parallel, spaced apart, vertically extending wing-like elements 303. The upper jaw 300 is disposed in the space or groove between the elements 303. The pivot pin 302 extends between the elements 303 of lower jaw 301 and through approximately the mid-point of the upper jaw 300. The upper jaw 300 is shaped to have an angulated lower surface which operates as a pivot or fulcrum.

In the rest position, as shown in FIG. 2, the spreader ends 310 and 311 of the upper and lower jaws, respectively, are disposed closely adjacent to each other. The relatively small spreader ends comprise projections or lips which extend from the front edge of the respective jaws. These lips are configured to extend inwardly of the rear slot or opening in the clip 102. The lips (or ends) 310 and 311 engage the inner surfaces of the respective clip.

In addition, the rear or tail end 312 of the lower jaw 301 is arranged to engage the crossbar end 237 of trigger 106. In a preferred embodiment, the tail end 393 includes a pair of parallel wing portions 312 for retaining the rod-like projection, i.e. crossbar 237, on the trigger. However, any other suitable arrangement of engagement between the trigger 106 and the lower jaw 301 is contemplated. The lower jaw also includes a resilient member or leaf spring 313 which is, effectively, attached in cantilever fashion to the rear portion of the lower jaw. The spring action is arranged to impinge upon a boss 314 or similar feature on the lower edge of the upper jaw so as to urge the rear portion of the upper jaw in the upward direction (as shown in the rest position in FIG. 2). This spring action causes the front end lips of the upper and lower jaws to be closely spaced in the rest position.

In addition, the lower jaw 301 includes an abutment 272 against which the front or forward end of the lower surface of the upper jaw abuts. The abutment 272 controls and regulates the minimum spacing between the lips of the upper and lower jaws whereby the inadvertent gripping of the patient's skin is avoided when the jaws are retracted (see infra).

The lower jaw 301 includes projections 315 (shown dashed) which extend from the sides thereof into a groove 316 or track which is formed in each of the sides (or halves) of the housing 103. This arrangement of projections (or track runners) provides a means for guiding the jaw mechanisms as they are moved by the trigger 106.

A ramp 375 is pivotally mounted to pivot pin 376. A resilient arm 378 extends from the pivot portion of ramp 375 and abuts boss 379 or similar structure. The arm 378 urges the ramp 375 downwardly within housing 103.

Ramp 375 includes a pair of spaced apart arms arranged on either side of the resilient arm 378. The arms 380 (see FIG. 4) are arranged to be disposed on either side of the upper jaw 300. A cross member 374 is connected to the ends of arms 380 and forms a bearing unit which limits upward movement of ramp 375 once sear members 350 have been disengaged from holding ramp downwardly during clip application, i.e. at end of trigger movement.

The sear member 350 (shown partially in dashed outline) is adapted to engage and latch the ends of arms 380 of ramp 375. The sear member pivots around pivot pin 551 and is controlled by leaf spring 352. The leaf spring 352 is attached to the sear member 350 adjacent to the pivot end thereof. The nether end of leaf spring 352 impinges upon a boss 353 formed in the side of handle 105 or housing 103. The leaf spring 352 is biased to urge the sear 350 in clockwise rotation around pivot 351 which may be formed in the housing 103. During the rest and the beginning portions of the clip application, sears 350 retain the ramp 375 in a downwardly position. While not obvious in FIG. 2, sear 350 may comprise a pair of substantially parallel sear members mounted on the pivot 351 with separate leaf springs 352.

Referring now to FIG. 3, there is shown a cross-sectional view of the apparatus in the operational state with the upper jaw 300 and lower jaw 301 moved outwardly relative to the front of the hemostasis applicator. Concurrently, as well, the jaws have moved a clip 102 outwardly and expanded the clip for use in the clipping process.

It is seen that the trigger 106 has been activated by being pulled to the right, relative to the support handle 105. The trigger 106 is pivoted around the pivot pin 235 in the housing. The spring 231 has been expanded and is under tension (whereby release of pressure on the trigger 106 will permit the spring to retract the trigger to the rest position).

Because of the movement of the trigger 106, the lower jaw 301 has been moved forwardly (to the left in FIG. 3). That is, pressure crossbar 237 has pushed against the tail end of lower jaw 300. The lips 310 and 311 of the upper and lower jaws, respectively, have previously been inserted into and engaged in the rear slot of clip 102 as the jaws moved forward. With the pressure applied to the jaws by the trigger 106, the jaws and clip, in combination, have moved to left, the locating arm 225 has been rotated slightly counterclockwise to move out of the way. That is, the lower edge of lower jaw 300 pushes on locator arm 225 which pivots about pivot 226 (against resilient arm 228). In addition, the door 108 has been caused to swing outwardly against the action of coil spring 220. Likewise, the clip 102 has moved outwardly on the end of the jaws. As the jaws are moved outwardly. Also, the tail bar 390 of upper jaw 301 slides down the side arms 380 of ramp 375 which is held steady by the action of sear 350. Consequently, the tail end of the upper jaw 300 moves closer to the tail end of the lower jaw 301. Conversely, the front ends of the upper and lower jaws tend to move apart as upper jaw 300 pivots about pivot bar 302. As a result, clip 102 is securely gripped before the door 108 is opened or the locator arms are moved.

The combination of this movement of the upper and lower jaws causes the clip 102 to be expanded and spread apart so that the rugose channel therein is separated and readied for application to a incised skin edge or the like.

As the movement of the jaws continues in response to continued pressure on trigger 106, the cross member 390 at the rear end of lower jaw 300 contacts the latching surface of sear 350. The sear 350 is moved out of engagement with the arms 380 of ramp 375. The ramp 375 is, thus, released and snaps upwardly in conjunction with and under the urging of tail bar 390 of upper jaw which is pushed upward by spring arm 313. This sudden release of ramp 375 permits the rear end of upper jaw 301 to freely move upwardly, as well. The spring arm 313 of lower jaw 300 also urges the rear end of the upper jaw upwardly. Thus, upper jaw 301 substantially pivots to the original position (especially as related to lower jaw 300). Consequently, the pressure on clip 102 by the jaws is relieved whereupon the clip assumes the closed (clamping) position.

Moreover, this snap-like movement of upper jaw 301 produces both a tactile and an aural indication to the operator that the clip is in place on the patient and has been released from the applicator. For example, the jaw ends snap together and produce an audible "click" when upper jaw 300 hits abutment 272. Thus, the procedure can be repeated. However, as noted above, the abutment 272 prevents the ends 310 an 311 of the upper and lower jaws, respectively, from touching each other.

At this juncture, pressure is released on trigger 106, tension spring 231 operates to pull the trigger 106 and, thus, the jaws 300 and 301 back to the rest condition. This action frees the sear 350 back into engagement with ramp 375. That is, the action of spring arm 313 (which may be stronger than spring arm 378) is reduced whereby spring arm 378 pushes ramp 375 downward to re-engage sear 350 then toil bar. 390 is all the way back to the rest position. Thus, the operational cycle can be repeated.

After placement of the clip on the wound surface, pressure is removed from the trigger 106 wherein the spring 231 retracts the trigger, and, concurrently, withdraws the jaw mechanisms back into the gun housing into substantially the rest position shown in FIG. 2. The gate 108 swings closed under the influence of spring 220. The locating arms 225 swing back into position. At this juncture, the pusher 211 and coiled leaf spring 210 in the magazine 201 force the series of clips 102 along the magazine wherein the next clip in line now engages the locating arm 225 and rests thereon for a repeat of the action noted above.

Referring now to FIG. 4, there is shown an exploded view of the internal, operative components of the invention. These components are identical to the components which bear similar reference numerals and which are shown and described relative to FIGS. 2 and 3 above. However, a more detailed showing of the individual components is provided in FIG. 4.

In FIG. 4, the trigger 106 is identical to the trigger 106 as shown and described above. The pivot pin 235 is shown extending beyond the planar surfaces of the internal portion 106A of the trigger. Eye 232 which is connected to one end of tension spring 231 is also depicted. The cross member or crossbar 237 is shown to extend from either side of the end of the inner portion of trigger 106. The crossbar 237 (in the form of a rod or cylinder) is intended to interact with the lower jaw 301 as shown and described above.

It is clear that the crossbar 237 (shown as a cylinder but other shapes are contemplated) is adapted to engage the tail end of the lower jaw 301. Thus, a compartment-like arrangement is provided at the back end of lower jaw 301. The compartment 393 includes rear walls 312 which form a slot 312A therebetween. The slot 312A is adapted to receive the relatively thin, inner portion of trigger 106. The rear walls 312 are adapted to engage the surface of the crossbar 237. In particular, when the trigger 106 is released from the active position (see FIG. 3) and moves to the rest position (see FIG. 2), the rod 237 bears against the rear walls 312 and, effectively, pulls the lower jaw 301 backwardly in the housing 103.

In similar fashion, the compartment 393 includes a front wall 412 against which the rod 237 bears when the trigger 106 is activated and moved from the rest position to the active position. The compartment has a somewhat trapezoidal shape for design purposes but is not limited thereto. In addition, rear track runners 391 in the form of planar wing-like elements protrude from the sides of the compartment. These "track-runners" are adapted to ride in the track 316 on the inner surface of the housing 103.

The resilient tongue or spring member 313 is mounted at the forward wall 412 of the compartment. The spring 313 is constructed so as to extend upwardly at an angle from the upper surface of the lower jaw 301. It will be seen that the spring 313 is adapted to apply a force to the the lower surface of upper jaw 300 in order to cause operation thereof as described above.

Also, the lower jaw 301 includes a pair of spaced apart, substantially vertical and parallel, wing-like members 303. The wing-like members are mounted at opposite sides of the body of the lower jaw 301. An aperture 302A passes through each of the wings 303 and is adapted to receive a pivot pin 302 which retains the upper jaw 300 within the lower jaw 301.

In addition, the front track runners 401 extend horizontally from the exterior surface of the wings 303. The track runners 401 are, essentially, co-planar with the rear track runners 391 at the rear of the lower jaw. Again, these track runners also engage and move in track 316. The front and rear track runners maintain the lower jaw 301 in the proper position within the housing 103 but permit motion backward and forward in a prescribed path.

The front end of the lower jaw includes the lip 311 which, as noted above, is adapted to engage the lower opening in the clip 102. The boss or abutment 272 extends upwardly from the upper surface of the main body of lower jaw 301 to provide the spacing required (and/or desired) between the upper and lower jaws at the end of the clip insertion process.

In the embodiment shown, the resilient leaf spring 313 can be molded as a single piece with the lower jaw apparatus. In addition, the lower jaw includes a pair of rearwardly extending arms which are extensions from the wings 303 to the rear compartment. Of course, any other arrangements or configurations of the lower jaw which will provide the functions shown and described may be appropriately used in the apparatus.

Also shown in FIG. 4 is the upper jaw 300 which has a generally elongated and inverted triangular configuration. The obtuse angle formed in the lower surface of jaw 300 provides a fulcrum for a pivotally rocking motion of the upper jaw 300. An aperture 302B is provided through the body of the upper jaw. The aperture 302B is adapted to receive a pivot pin 302 as discussed supra.

The width of the front portion of upper jaw 300 is defined to fit snugly between the wings 303 without binding thereto. By an appropriate fit, the upper jaw 300 will tend to not wobble or become misaligned in the apparatus.

Lip 310 at the front end of the upper jaw, is adapted to engage a clip 102 as noted above.

The rearward portion of upper jaw 300 is somewhat narrower than the forward portion in order to more properly fit within the ramp 375 described infra. A boss 314 in the nature of a bump or the like extends from one of the angulated lower surfaces of the upper jaw 300 and provides a bearing point for the leaf spring 313 in the lower jaw.

A crossbar 390 extends outwardly from the sides of the tail end of upper jaw 300. In the configuration shown, the crossbar 390 is substantially cylindrical in configuration. However, of course, other configurations are contemplated. As will be seen, the crossbar 390 bears against the under surface of ramp 375 and is positioned thereby.

The ramp 375 includes an upper surface 381 and two side portions 380 which depend therefrom. The upper surface 381 is appropriately cut and formed to include a leaf spring 378 which is adapted to bear against the boss 379 (see FIGS. 2 and 3). A pivot pin 376 extends from the outer surfaces of the ramp 375 and is adapted to be mounted in an appropriate mounting aperture in housing 103. The front end of the ramp 375 is formed by a cross member 374 which extends upwardly and over the space between the side walls of the ramp. The groove 402 in the under surface of cross member 374 is adapted to substantially conform to the width of the rear portion of upper jaw 300 in order to provide a reasonably loose fit which permits easy travel of the respective parts.

The space between the side walls of ramp 374 is adapted to receive the cross bar 390 of upper jaw 300 and to control the positioning thereof (in a side-to-side manner). In essence, the leaf spring 378 bears on the boss 379 thereby forcing the ramp downwardly. The tail end 390 of upper jaw 300 is forced downwardly along the slope of the ramp (see FIGS. 2 and 3) as the upper and lower jaw are moved forwardly in response to operation of the trigger 106.

The sear 350 latch (and the counterpart sear 350A) are mounted on a pivot pin 351 which is mounted in the housing 103. The sear 350 is mounted behind the forward track runner 401 on the lower jaw 301. The spring arms 352 (and 352A) bear upon the boss 353 in housing 103. The upper portion of the sear 350 includes a lip 404 which engages the upper surface 381 of ramp 375. As a consequence, the ramp 375 is maintained in the downwardly sloping position shown in FIGS. 2 and 3. Thus, crossbar 390 at the tail end of upper jaw 300 also follows this ramp direction.

Thus, when the trigger 106 is moved and pushes lower jaw 301 forwardly, upper jaw 300 which is carried therewith and the forward edge of wing 391 bears against the curved surfaces of each sear 350. The sear 350 is moved forwardly and, effectively, pivots around the pivot pin 351. As the sear moves forwardly, or rotates counterclockwise, the lip 404 is disengaged from the forward edge of the ramp 375. When the sear 350 is removed, the ramp 375 snaps upwardly in response to the force supplied on the crossbar 390 of upper jaw 300. Likewise, leaf spring 313 bears against the rear portion of upper jaw 300 which also moves upwardly along with the ramp 375. When the rear portion of the upper jaw 300 moves upwardly, the forward end snaps downwardly and, thus, releases the clip 102 which had been mounted thereon.

When trigger 106 is released, the lower jaw 301 is drawn backward thereby and carries upper jaw 300 therewith. Likewise, sear 350 is permitted to rotate in the clockwise direction (as seen in the drawings) as a result of the spring-loaded arm 352. The sear operates to re-engage the forward edge of the side panels of the ramp 375 which is forced downwardly by the resilient spring 378. The apparatus re-assumes the rest position shown in FIG. 2 and is ready for operation again when the trigger 106 is activated by the operator of the clip applicator.

Referring now to FIG. 5, there is shown a cross-sectional view of the magazine 101 taken along the lines 5—5 in FIG. 2. This Figure shows the arrangement of a clip 102 in the magazine 101. In particular, the rugose ends or edges 704 are in the top position while the jaw receiving the aperture 701 is in the bottom position.

The shoulder 702 of the clip rests and rides on the ledge 125 in the side wall 203 of the magazine. Likewise, the groove 213 is shown in each of the side walls 203. The leaf spring 210 is shown, in cross-section, resting upon the lower track 202 of the magazine.

Referring now to FIG. 6, there is shown a cross-sectional view of the magazine 101 taken along the lines 6—6 in FIG. 1. Again, the upper and lower tracks of the magazine 101 are depicted. The cross-sectional view of the leaf spring 210, disposed on the lower track 202 is provided. In this case, the pusher 211 is shown along with the groove 211A at the rear portion thereof for receiving a coiled portion of the spring 210. The pin 212 which extends from each side of the pusher 211 is shown resting in the groove 213 which controls the movement of the pusher 211.

Referring now to FIGS. 7 through 9 inclusive, there are shown several views of the improved clip 102 which is used with the instant invention. As noted above, this clip is am improved variation on a Raney clip.

It is seen that the clip 102 has a somewhat ovoid configuration. Typically, the clamp is made of a plastic such as nylon, Delrin or any other suitable material. A space or opening 701 is provided at the bottom end of the clip. This opening (or aperture) has a generally rectilinear configuration and can be accessed by forceps in an individual clip utilization process. Conversely, the opening 701 is accessed by the lips 310 and 311 of the jaws 300 and 301 of the hemostasis clip gun of the instant invention.

Also, the clip 102 includes a shoulder 702 at each side thereof. This shoulder rests on the ledge 125 in the wall thereof of magazine 101 thereby maintaining correct orientation of the clip. Also, as the clip 102 enters the housing 103 from the magazine 100, it follows similar aligning shoulders 325 in each half of housing 103 to keep the clip aligned as it slips over lips 310 and 311.

The opposite, slightly narrower end of the clip includes a gap 703 between the edges 704 and 705 of the clip. These edges are, preferably, rugose or serrated in order to provide a better gripping action when the clip is in use.

When the jaws 300 and 301 are inserted into the opening 701 and activated, the clip tends to open or expand as shown by the dashed outlines 102A in FIG. 9. However, the clips are fabricated so that the plastic has a "memory" and tends to return to the original shape shown, after it has been expanded and the appropriate skin or wound margins have been inserted therein.

Thus, there is shown and described a unique design and concept of a hemostasis clip applicator. The particular configuration shown and described herein relates to a configuration for an automatic, series feed application. While this description is directed to a particular embodiment, it is understood that those skilled in the art may conceive modifications and/or variations to the specific embodiments shown and described herein. For example, the precise configuration of the jaws; the interconnection between the jaws and the trigger; the arrangement of the spring-loading mechanisms and so forth can all be modified, if desired. However, any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A clip applicator comprising,
    first housing means for storing a plurality of clips,
    second housing means including jaw means which are selectively expandable,
    said first housing means disposed in engagement with said second housing means and adapted to selectively supply individual clips to said jaw means whereby said clips can be selectively expanded by said jaw means, and
    ramp means mounted in said second housing means,
    said jaw means mounted in sliding relationship to said ramp means whereby said jaw means is selectively expanded.

2. The clip applicator recited in claim 1 including,
    resilient means in said first housing means for urging said clips in a prescribed direction.

3. The clip applicator recited in claim 1 including,
    trigger means mounted in said second housing means and adapted to engage said jaw means.

4. The applicator recited in claim 3 wherein,
    said trigger means is pivotally mounted to said second housing and selectively causes said jaw means to slide relative to said second housing when said trigger means is actuated.

5. The clip applicator recited in claim 2 wherein,
    said resilient means comprises a coiled spring.

6. The clip applicator recited in claim 2 wherein,
    said resilient means is connected to one end of said first housing means.

7. The clip applicator recited in claim 1 wherein,
    said jaw means includes a first jaw member and a second jaw member,
    said first and second jaw members pivotally mounted to each other.

8. The clip applicator recited in claim 1 including,
door means at the front end of second housing means through which clips are selectively passed by said jaw means.

9. The clip applicator recited in claim 8 wherein,
said door means is spring loaded to the closed position at the front end of said second housing.

10. The clip applicator recited in claim 1 including,
sear means pivotally mounted in said second housing means,
said sear means adapted to selectively engage said ramp means thereby to position said ramp means relative to said jaw means.

11. The applicator recited in claim 1 wherein,
said first housing has a generally rectilinear cross-section.

12. The applicator recited in claim 11 wherein,
said first housing is curved at one end thereof to direct the clips stored therein in a preferred direction.

13. The applicator recited in claim 12 wherein,
said first housing is latched to said second housing so that clips stored in said first housing are selectively transferred into said second housing.

14. The applicator recited in claim 12 wherein,
said second housing has a stepped configuration to accommodate said curved first housing.

15. The cips applicator recited in claim 1 wherein,
said clips are independent of each other.

16. The clip applicator recited in claim 1 wherein,
said clips are hemostasis clips.

17. The clip applicator recited in claim 1 wherein,
said ramp means is pivotally mounted within said second housing.

18. The clip applicator recited in claim 17 wherein,
said ramp means includes resilient means to selectively force said ramp means downwardly relative to said second housing.

19. A clip applicator comprising,
a magazine for retaining a plurality of resilient clips,
a support device for supporting said magazine thereon, and
a pair of opposed jaws slidably mounted at said support device,
said pair of opposed jaws adapted to engage individual clips and to expand relative to said support device thereby to expand said clips.

20. The applicator recited in claim 19 wherein,
said clips include an aperture in a closed end thereof which receives said pair of opposed jaws.

21. The applicator recited in claim 19, wherein,
each of said jaws include a lip which extends from the end thereof and engages said clips.

22. The applicator recited in claim 19 wherein,
said pair of opposed jaws extend beyond said support device when in engagement with said clips.

23. The applicator recited in claim 19 including,
clip locator means mounted in said support device to receive clips from said magazine and position same relative to said pair of opposed jaws.

24. The applicator recited in claim 23 wherein,
said clip locator means is spring loaded into position to receive said clips,
said clip locator means is pivotally mounted to be selectively moved out of said position when said jaws slide relative to said support device.

25. The applicator recited in claim 19 including,
latch means for selectively attaching said magazine to said support device.

26. The applicator recited in claim 19 wherein,
said magazine includes a ledge formed in at least one sidewall thereof for cooperating with said clips in order to maintain said clips in a preferred orientation.

27. The applicator recited in claim 26 wherein,
said clips include a shoulder at at least one side thereof to cooperate with said ledge.

28. The applicator recited in claim 19 wherein,
said pair of opposed jaws is pivotally mounted to each other.

29. The applicator recited in claim 28 includes,
a spring member interposed between said pair of opposed jaws to urge the front end of said jaws toward each other.

30. The applicator recited in claim 19 including,
spacer means interposed between said pair of opposed jaws to determine the minimum spacing therebetween.

31. Clip means comprising,
a coiled sheet of resilient material having a closed end, an open end with abutting edges and a pair of substantially parallel sides between said open and closed ends,
said abutting edges having at least a portion thereof which is rugose,
said closed end having an aperture therethrough, and
an idented shoulder in at least one of said sides of said coiled sheet, intermediate said closed end and open end.

32. The clip means recited in claim 31 wherein,
said abutting edges are spaced apart.

33. The clip means recited in claim 31 wherein,
said coiled sheet of resilient material has a generally ovoid configuration.

* * * * *